(12) United States Patent
Al-Mulla et al.

(10) Patent No.: US 10,087,487 B2
(45) Date of Patent: Oct. 2, 2018

(54) METHOD FOR DETERMINING RISK OF METASTATIC RELAPSE IN A PATIENT DIAGNOSED WITH COLORECTAL CANCER

(71) Applicant: KUWAIT UNIVERSITY, Safat (KW)

(72) Inventors: Fahd Al-Mulla, Yarmouk (KW); Jean Paul Thiery, Singapore (SG); Milad S. Bitar, Salmiya (KW)

(73) Assignee: KUWAIT UNIVERSITY, Safat (KW)

( * ) Notice: Subject to any disclaimer, the term of this patent is extended or adjusted under 35 U.S.C. 154(b) by 557 days.

(21) Appl. No.: 14/481,884

(22) Filed: Sep. 9, 2014

(65) Prior Publication Data

US 2016/0068912 A1   Mar. 10, 2016

(51) Int. Cl.
*C12P 19/34*   (2006.01)
*C12Q 1/6886*   (2018.01)

(52) U.S. Cl.
CPC ...... *C12Q 1/6886* (2013.01); *C12Q 2600/118* (2013.01); *C12Q 2600/158* (2013.01)

(58) Field of Classification Search
USPC ..................................... 435/6.11, 6.12, 91.2
See application file for complete search history.

(56) References Cited

U.S. PATENT DOCUMENTS

| | | | |
|---|---|---|---|
| 8,211,634 B2 | 7/2012 | DePinho et al. | |
| 8,498,822 B2 | 7/2013 | Semizarov et al. | |
| 2009/0246789 A1* | 10/2009 | Buckhaults | C12Q 1/6886 435/6.14 |
| 2009/0275057 A1 | 11/2009 | Linke et al. | |
| 2011/0059464 A1 | 3/2011 | Muraca | |
| 2011/0257034 A1* | 10/2011 | Barany | G01N 33/57419 506/9 |
| 2012/0077694 A1 | 3/2012 | Gray et al. | |
| 2012/0220478 A1* | 8/2012 | Shaffer | C12Q 1/6886 506/9 |

FOREIGN PATENT DOCUMENTS

EP   2 669 682 A1   12/2013

OTHER PUBLICATIONS

Fahd Al-Mulla et al., "Genetic Profiling of Stage I and II Colorectal Cancer May Predict Metastatic Relapse," Modern Pathology 19: 648-58 (2006).

Robert N. Jorissen et al., "Metastasis-Associated Gene Expression Changes Predict Poor outcomes in Patients with Dukes Stage B and C Colorectal Cancer," Clininal Cancer Research (24)15: 7642-7651 (2009).

* cited by examiner

*Primary Examiner* — Kenneth R Horlick
(74) *Attorney, Agent, or Firm* — Richard C. Litman

(57) ABSTRACT

The method for determining risk of metastatic relapse in a patient diagnosed with colorectal cancer (CRC) can include detecting a level of at least one indicator of metastatic potential in a biological sample from the patient, comparing the level of the indicator of metastatic potential with a control, and identifying the patient as one who is at risk of metastatic relapse and a candidate for chemotherapy if an aberrant level of the indicator of metastatic potential in the biological sample compared to the control is detected. The at least one indicator of metastatic potential can include at least one metastasis-inducing gene and/or at least one metastasis suppressor gene. An aberrant level of the at least one indicator of metastatic potential can include a copy number gain of the metastasis-inducing gene and/or a copy number loss of the metastasis-suppressor gene.

5 Claims, 4 Drawing Sheets

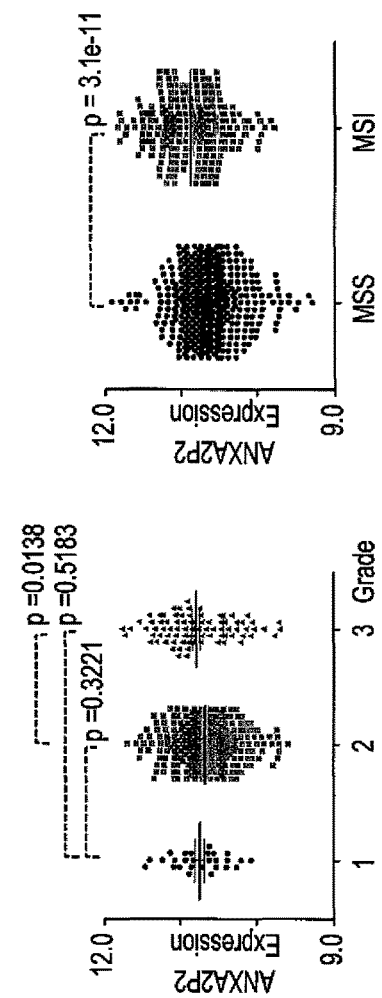
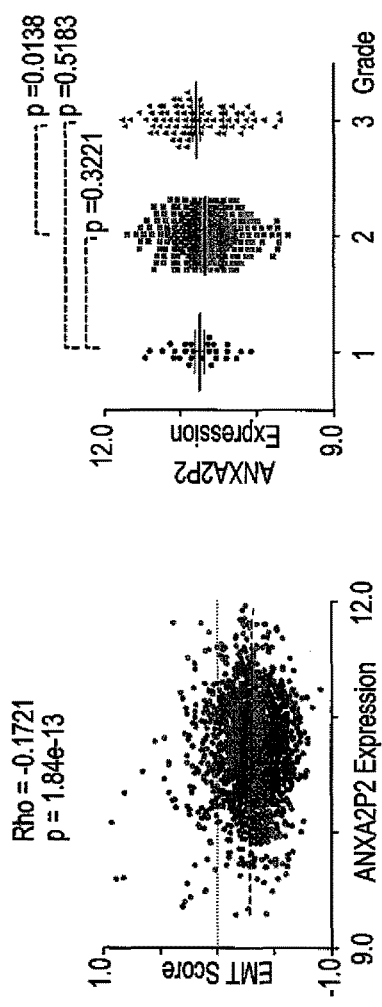
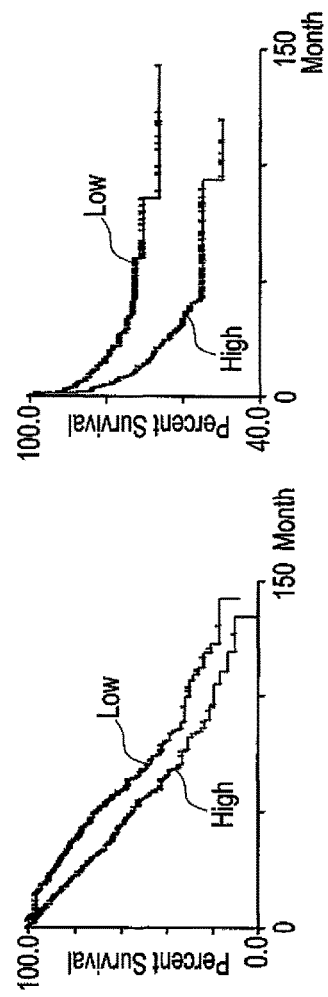
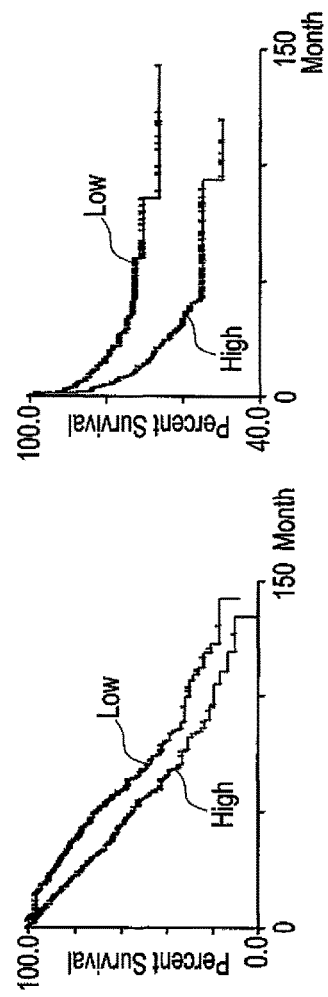
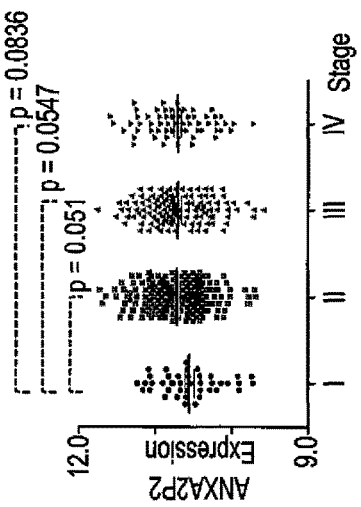

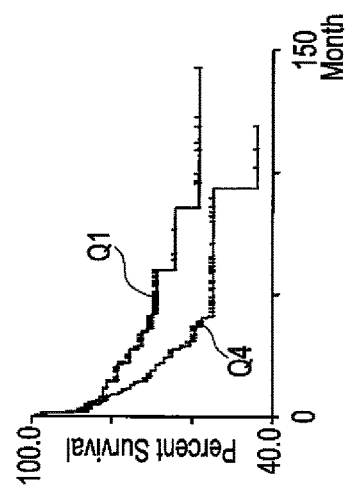
Fig. 8
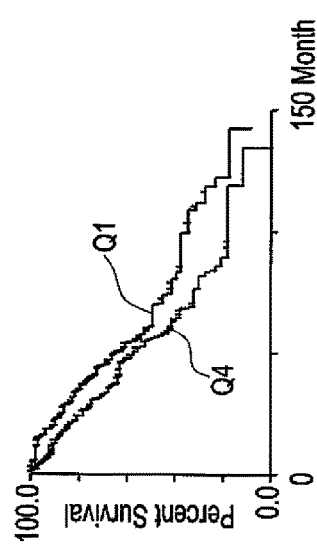
Fig. 9
Fig. 10
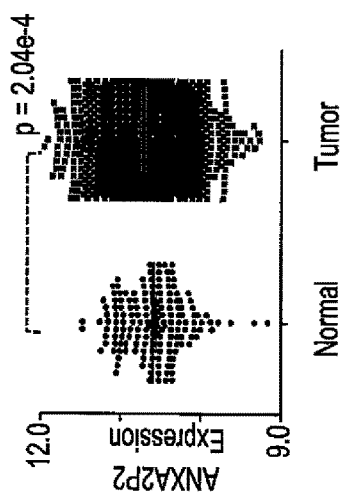
Fig. 11
Fig. 12
Fig. 13

METHOD FOR DETERMINING RISK OF METASTATIC RELAPSE IN A PATIENT DIAGNOSED WITH COLORECTAL CANCER

BACKGROUND OF THE INVENTION

1. Field of the Invention

The present invention relates to methods of diagnosing and treating cancer, and particularly to a method for determining risk of metastatic relapse in a patient diagnosed with colorectal cancer by screening colorectal cancer patients for aberrant levels of at least one of 42 genes identified as markers of likely metastatic occurrence, and subsequently treating the patient.

2. Description of the Related Art

Colorectal cancer (CRC) is one of the most common cancers in the world. Early detection and surgery with excision of the tumor is currently of critical importance for a successful treatment. For localized tumors, i.e. tumors that have not evolved into a metastasizing disease, surgical intervention with radical resection of the tumor and surrounding bowel and tissues is performed. Colorectal tumors are categorized into several stages according to Dukes' stages A-D or more recently according to the TNM classification. Early stage tumors (Dukes' stages A and B) are generally associated with a relatively favorable outcome, while later stage tumors, presenting with metastasis (Dukes' stage C and D) have poor survival rates. Unfortunately, metastasis often goes undetected until the tumor has grown to a considerable size. The tumor typically metastasizes to regional lymph nodes, but distant metastasis to the liver and lung are also common.

Patients with early-stage CRC (Stage I and II or Dukes' A and B) undergo surgical resection only and are not treated chemotherapeutically. Almost one fourth of early stage patients with non-metastatic disease, however, relapse with metastasis later, Patients diagnosed with metastatic forms of CRC, namely stages Dukes' C with lymph node metastasis and Dukes' D with hematological dissemination, have five year survival rates of 37% and 11%, respectively. Patients diagnosed at an early stage (Dukes' A and B) with no evidence of metastatic disease at time of surgery have a significantly better prognosis featuring five-year survival rates of 85% and 67%, respectively (Cancer Research UK, 2004). However, a significant proportion of these patients (10-45%) relapse with metastatic disease.

Chemotherapy has proven effective for Dukes' C stage tumors. Newer studies also indicate the value of chemotherapy for some patients with early colorectal cancer at risk of metastatic relapse. However, although chemotherapeutic intervention has been implemented for some patients with early colon cancer, its implementation as a routine treatment is not cost effective and can be counterproductive. The side effects associated with the treatment, in particular, make it desirable to avoid application of chemotherapy except in cases of high relapse risk.

Identifying patients at high risk of metastatic relapse from CRC would be useful to target treatment to only those patients, and thereby avoid overtreatment. Suitable markers for identifying this population are currently lacking.

Thus, a method for determining risk of metastatic relapse in a patient diagnosed with colorectal cancer solving the aforementioned problems is desired.

SUMMARY OF THE INVENTION

The method for determining risk of metastatic relapse in a patient diagnosed with colorectal cancer (CRC) can include detecting a level of at least one indicator of metastatic potential in a biological sample from the patient, comparing the level of the indicator of metastatic potential with a control, and identifying the patient as one who is at risk of metastatic relapse and a candidate for chemotherapy if an aberrant level of the indicator of metastatic potential in the biological sample compared to the control is detected. The at least one indicator of metastatic potential can include at least one metastasis-inducing gene and/or at least one metastasis suppressor gene. The metastasis-inducing gene can include CDC42BPA, VLDLR, GLIS3, MPDZ, SMU1, ANXA2P2, SCEL, DUSP14, USP32, PITPNC1, SEMG1, DOK5, or ING1. The metastasis-suppressor gene can include ZNF366, C5orf48, CSMD1, NAT1, NAT2, SPAG11A, ADRA1A, EPHX2, ZNF703, BRF2, RAB11FIP1, ADRB3, WDR5, DIO3, ONECUT1, C20orf202, SIRPD, ADRA1D, MCM8, LOC339593, GP1BB, CABIN1, TOP1P2, ZNRF3, KIAA1656, APOBEC3D, CACNA1I, FAM83F, or PCDHGA11. An aberrant level of the at least one indicator of metastatic potential can include a copy number gain in the metastasis-inducing gene and/or a copy number loss of the metastasis-suppressor gene.

These and other features of the present invention will become readily apparent upon further review of the following specification and drawings.

BRIEF DESCRIPTION OF THE DRAWINGS

FIG. 2 is a graph showing the correlation between ANXA2P2 gene expression and clinicopathological association with EMT.

FIG. 3 is a graph showing the correlation between ANXA2P2 gene expression and clinicopathological association with tumor grade.

FIG. 4 is a graph showing the correlation between ANXA2P2 gene expression and clinicopathological association with microsatellite instability.

FIG. 5 is a graph showing the correlation between ANXA2P2 gene expression and clinicopathological association with CRC stage.

FIG. 6 is a graph showing the correlation between ANXA2P2 gene expression and clinicopathological association with overall (disease specific) survival (Kaplan-Meier survival log-rank test).

FIG. 7 is a graph showing the correlation between ANXA2P2 gene expression and clinicopathological association with disease-free survival (Kaplan-Meier survival log-rank test).

FIG. 8 is a graph showing the correlation between ANXA2P2 gene expression and clinicopathological association with normal colon vs. CRC tumor.

FIG. 9 is a graph showing the correlation between ANXA2P2 gene expression and clinicopathological association with overall (disease specific) survival (Kaplan-Meier survival log-rank test).

FIG. 10 is a graph showing the correlation between ANXA2P2 gene expression and clinicopathological association with disease-free survival (Kaplan-Meier survival log-rank test).

FIG. 11 is a graph showing the correlation between Nat1 gene expression and clinicopathological association with EMT.

FIG. 12 is a graph showing the correlation between Nat1 gene expression and clinicopathological association with tumor grade.

FIG. 13 is a graph showing the correlation between NAT1 gene expression and clinicopathological association with microsatellite instability.

Similar reference characters denote corresponding features consistently throughout the attached drawings.

DETAILED DESCRIPTION OF THE PREFERRED EMBODIMENTS

Figure 1:
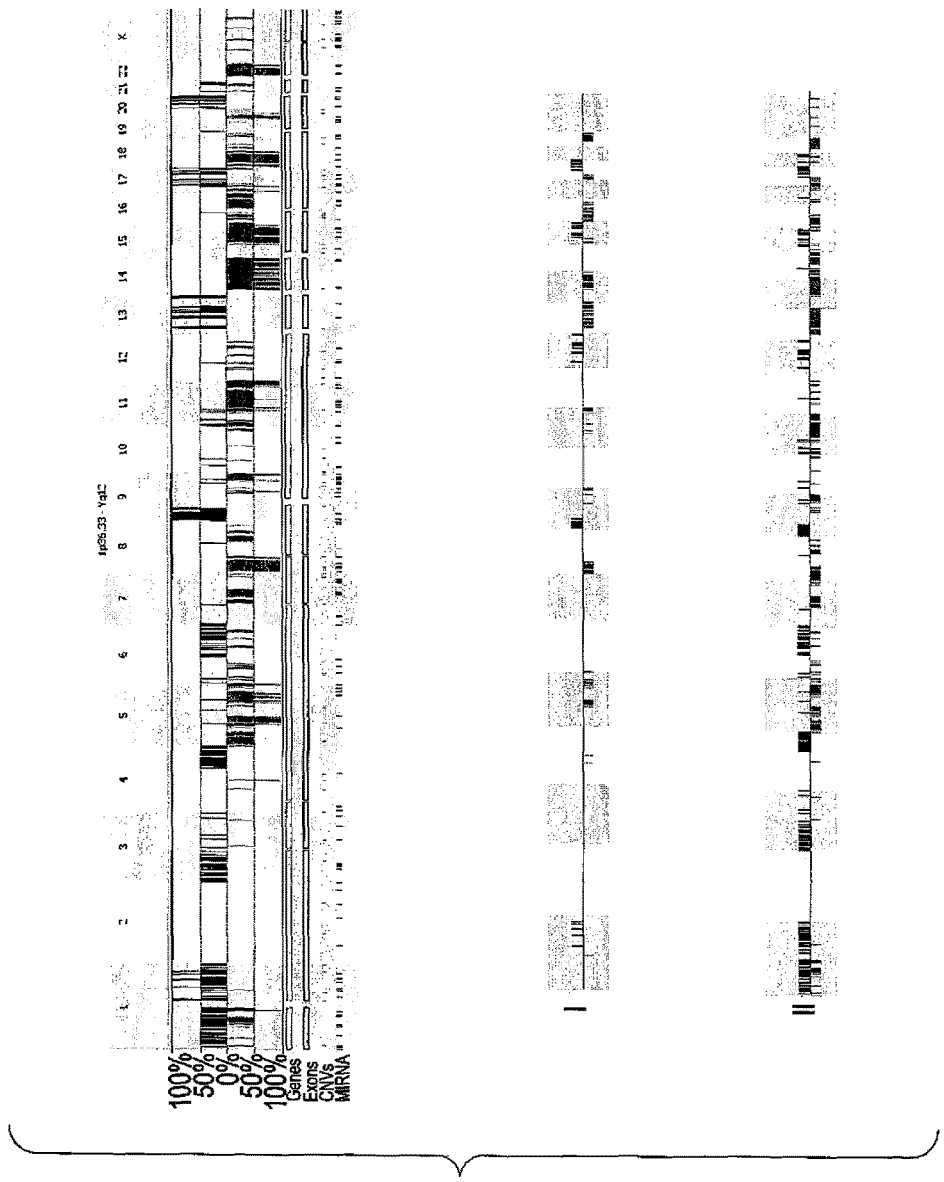
FIG. 1 is a chart correlating genomic copy number variations to corresponding chromosomes.

The method for determining risk of metastatic relapse in a patient diagnosed with colorectal cancer (CRC) can include detecting the level of at least one indicator of metastatic potential in a biological sample from the patient, comparing the level of the indicator of metastatic potential with a control, and identifying the patient as one who is at risk of metastatic relapse and a candidate for chemotherapy if an aberrant level of the indicator of metastatic potential in the biological sample compared to the control is detected. The indicator of metastatic potential can include a metastasis-inducing gene and/or a metastasis suppressor gene. The metastasis-inducing gene can include CDC42BPA, VLDLR, GLIS3, MPDZ, SMU1, ANXA2P2, SCEL, DUSP14, USP32, PITPNC1, SEMG1, DOK5, or ING1. The metastasis-suppressor gene can include ZNF366, C5orf48, CSMD1, NAT1, NAT2, SPAG11A, ADRA1A, EPHX2, ZNF703, BRF2, RAB11FIP1, ADRB3, WDR5, DIO3, ONECUT1, C20orf202, SIRPD, ADRA1D, MCM8, LOC339593, GP1BB, CABIN1, TOP1P2, ZNRF3, KIAA1656, APOBEC3D, CACNA1I, FAM83F, or PCDHGA11.

Detecting the level of the at least one indicator of metastatic potential in the biological sample can include measuring a copy number variation (CNV) of the at least one indicator of metastatic potential. An aberrant level of the indicator of metastatic potential can include a copy number gain in the metastasis-inducing gene and/or a copy number loss of the metastasis-suppressor gene. An aberrant level of the at least one indicator of metastatic potential in the biological sample can include a copy number gain in more than one metastasis-inducing gene, for example, two or more, three or more, four or more, or five or more of the metastasis-inducing genes. An aberrant level of the indicator of metastatic potential in the biological sample can include a copy number loss in more than one metastasis-suppressor gene, for example, two or more, three or more, four or more, or five or more of the metastasis-suppressor genes.

An aberrant level of the at least one indicator of metastatic potential in the biological sample can include a copy number gain of one or more of the metastasis-inducing genes and a copy number loss of one or more of the metastasis-suppressor genes. An aberrant level of the indicator of metastatic potential in the biological sample can include a copy number gain of all of the metastasis-inducing genes and a copy number loss of all of the metastasis-suppressor genes. For example, a biological sample having a copy number gain of CDC42BPA, VLDLR, GLIS3, MPDZ, SMU1, ANXA2P2, SCEL, DUSP14, USP32, PITPNC1, SEMG1, DOK5, and ING1, and a copy number loss of ZNF366, C5orf48, CSMD1, NAT1, NAT2, SPAG11A, ADRA1A, EPHX2, ZNF703, BRF2, RAB11FIP1, ADRB3, WDR5, DIO3, ONECUT1, C20orf202, SIRPD, ADRA1D, MCM8, LOC339593, GP1BB, CABIN1, TOP1P2, ZNRF3, KIAA1656, APOBEC3D, CACNA1I, FAM83F, and PCDHGA11 can indicate that the patient is at risk of metastatic relapse and a candidate for chemotherapy.

Detecting the level of the at least one indicator of metastatic potential in the biological sample can include measuring a gene expression product of the at least one indicator of metastatic potential. For example, detecting the level of the at least one indicator of metastatic potential in the biological sample can include measuring a gene expression product of the metastasis-inducing gene, and/or a gene expression product of the metastasis suppressor gene.

An aberrant level of the indicator of metastatic potential can include an increased level of a gene expression product of at least one metastasis-inducing gene that can be correlated with a copy number gain of the at least one metastasis-inducing gene and/or a decreased level of a gene expression product of at least one metastasis-suppressor gene that can be correlated with a copy number loss of the at least one metastasis-suppressor gene. An aberrant level of the indicator of metastatic potential in the biological sample can include increased levels of gene expression products of more than one metastasis-inducing gene, which can be correlated with copy number gains in the corresponding metastasis-inducing genes. An aberrant level of the indicator of metastatic potential in the biological sample can include levels of gene expression products of more than one metastasis-suppressor gene, which can be correlated with a copy number loss in the respective metastasis-inducing genes.

An increased level in a gene expression product of one or more metastasis-inducing genes and decreased level in a gene expression product of one or more metastasis-suppressor genes can be any measurable increase or decrease in expression, respectively, that can be correlated with the copy number variations identified in Table 1. In some embodiments, the increase or decrease in expression is about 1.5-fold, about 2-fold, about 2.5-fold, about 3-fold, about 4-fold, about 5-fold, about 7-fold or about 10-fold. As described below, the gene expression products can be detected using any one of a number of methods well known in the art. Expression of either mRNA or protein is contemplated herein.

The present inventors have determined that a copy number gain of one or more metastasis-inducing genes and/or a copy number loss of one or more metastasis-suppressor genes can be used to identify patients with CRC who are at risk of metastatic relapse. Thus, a copy number gain or loss in the metastasis-inducing genes and metastasis-suppressor genes, respectively, can provide genetic markers to identify CRC patients at risk of metastatic relapse.

The method for determining risk of metastatic relapse in a patient diagnosed with colorectal cancer (CRC) can include detecting a level of more than one indicator of metastatic potential in a biological sample from the patient. For example, a level of more than one metastasis-inducing gene or more than one metastasis-suppressor gene can be detected. A level of at least one metastasis-inducing gene and at least one metastasis-suppressor gene can be detected. A level of gene expression products of more than one metastasis-inducing gene or more than one metastasis-suppressor gene can be detected. A level of gene expression products of at least one metastasis-inducing gene and at least one metastasis-suppressor gene can be detected.

Table 1 provides the genetic markers for CRC patients at risk of metastatic relapse, including the metastasis-inducing genes and metastasis-suppressor genes, the corresponding chromosomal regions of the genes, and the copy number variation, e.g., the copy number gain or copy number loss, for each of the genes that can identify a human patient as one who is at risk of metastatic relapse and a candidate for chemotherapy. Gene locations in Table 1 were determined using human genome version 19 assembly (hg19 assembly). The genome browser available at the National Center for Biotechnology Information (NCBI) website and the genome browser available at the website of the Department of Molecular Medicine (MOMA) at Aarhus University, Denmark (a mirror to the UCSC genome browser) were used to identify gene location.

TABLE 1

| Region | Cytoband Location | CNV Event | Gene Symbols |
|---|---|---|---|
| chr1: 223, 586, 936-223, 618, 129 | q42.13 | Gain | CDC42BPA |
| chr5: 71, 478, 793-72, 228, 866 | q13.2 | Loss | ZNF366 |
| chr5: 125, 906, 988-126, 007, 887 | q23.2 | Loss | C5orf48 |
| chr5: 140, 800, 537-140, 892, 546 | q31.3 | Loss | PCDHGA11 |
| chr8: 3, 192, 664-3, 298, 863 | p23.2 | Loss | CSMD1, SPAG11A |
| chr8: 18, 105, 847-18, 347, 740 | p22 | Loss | NAT1, NAT2 |
| chr8: 26, 337, 410-28, 069, 477 | p21.2-p21.1 | Loss | ADRA1A, EPHX2 |
| chr8: 37, 553, 512-38, 049, 159 | p12 | Loss | ZNF703, BRF2, RAB11FIP1, ADRB3 |
| chr9: 1, 934, 152-3, 256, 829 | p24.3-p24.2 | Gain | VLDLR |
| chr9: 3, 272, 788-10, 248, 806 | p24.2-p23 | Gain | GLIS3 |
| chr9: 13, 084, 687-13, 177, 901 | p23 | Gain | MPDZ |
| chr9: 32, 501, 115-33, 201, 863 | p21.1-p13.3 | Gain | SMU1 |
| chr9: 33, 580, 807-33, 694, 356 | p.13.3 | Gain | ANXA2P2 |
| chr9: 133, 977, 094-134, 047, 962 | q34.2 | Loss | WDR5 |
| chr13: 77, 091, 913-77, 120, 617 | q22.3 | Gain | SCEL |
| chr13: 111, 365, 083-111, 373, 421 | q34.2 | Gain | ING1 |
| chr14: 100, 622, 842-101, 449, 140 | q32.31 | Loss | DIO3 |
| chr15: 50, 826, 333-50, 843, 466 | q21.3 | Loss | ONECUT1 |
| chr17: 32, 784, 580-33, 098, 353 | q12 | Gain | DUSP14 |
| chr17: 55, 661, 447-55, 682, 369 | q23.2 | Gain | USP32 |
| chr17: 62, 823, 228-62, 982, 920 | q24.2 | Gain | PITPNC1 |
| chr20: 604, 610-1, 511, 702 | p13 | Loss | C20orf202, SIRPD |
| chr20: 4, 163, 287-4, 643, 781 | p13 | Loss | ADRA1D |
| chr20: 5, 748, 138-7, 167, 999 | p12.3 | Loss | MCM8 |
| chr20: 7, 910, 186-12, 535, 405 | p12.3-p12.1 | Loss | LOC339593 |
| chr20: 43, 182, 807-43, 715, 277 | q13.12 | Gain | SEMG1 |
| chr20: 52, 091, 103-52, 625, 110 | q13.2 | Gain | DOK5 |
| chr22: 18, 008, 241-18, 116, 460 | q11.21 | Loss | GP1BB |
| chr22: 22, 722, 828-22, 886, 439 | q11.23 | Loss | CABIN1 |
| chr22: 23, 451, 589-23, 676, 351 | q11.23 | Loss | TOP1P2 |
| chr22: 27, 750, 436-27, 757, 126 | q12.1 | Loss | ZNRF3 |
| chr22: 29, 051, 285-29, 095, 047 | q12.2 | Loss | KIAA1656 |

TABLE 1-continued

| Region | Cytoband Location | CNV Event | Gene Symbols |
|---|---|---|---|
| chr22: 37, 735, 270-37, 795, 940 | q13.1 | Loss | APOBEC3D |
| chr22: 37, 822, 564-39, 067, 017 | q13.1 | Loss | CACNA1I, FAM83F |

Chromosomal regions identified in Table 1 that are involved in copy number gain induced expression of the corresponding metastasis-inducing genes (CDC42BPA, VLDLR, GLIS3, MPDZ, SMU1, ANXA2P2, SCEL, DUSP14, USP32, PITPNC1, SEMG1, DOK5, ING1). Chromosomal regions identified in Table 1 involved in copy number loss resulted in the loss or reduced expression of the corresponding metastasis-suppressor genes (ZNF366, C5orf48, CSMD1, NAT1, NAT2, SPAG11A, ADRA1A, EPHX2, ZNF703, BRF2, RAB11FIP1, ADRB3, WDR5, DIO3, ONECUT1, C20orf202, SIRPD, ADRA1D, MCM8, LOC339593, GP1BB, CABIN1, TOP1P2, ZNRF3, KIAA1656, APOBEC3D, CACNA1I, FAM83F, PCDHGA11).

Detection of a copy number variation (CNV) (as reflected in Table 1) in a biological sample from an early stage CRC patient and/or a change in expression that can be correlated with a copy number variation in Table 1 can yield significant prognostic measurements, e.g., identification of CRC patients that are at risk of metastatic relapse or have metastatic potential. A patient at risk of metastatic relapse can be a candidate for chemotherapy and/or other appropriate therapy known in the art to prevent or treat metastasis. Accordingly, the present methods for determining risk of metastatic relapse in a patient diagnosed with early stage colorectal cancer (CRC) can allow physicians to customize the treatment of colorectal cancer to the needs of individual patients, thereby maximizing the benefit of treatment and minimizing the exposure of patients to unnecessary treatments which do not provide, any significant benefits and often carry serious risks due to toxic side-effects.

A copy number gain in DNA copy number of one or more metastasis-inducing genes and/or a loss in DNA copy number of one or more metastasis-suppressor genes can be associated with a poor prognosis. A copy number loss in DNA copy number of one or more metastasis-inducing genes and/or a gain in DNA copy number of one or more metastasis-suppressor genes can be associated with a good prognosis. High expression of at least one metastasis-inducing gene in a patient sample that can be correlated with a copy number gain of the at least one metastasis-inducing gene, can be associated with a poor prognosis. Low expression of at least one metastasis-inducing gene in a patient sample that can be correlated with a copy number loss of the at least one metastasis-inducing gene, can be associated with a good prognosis. High expression of at least one metastasis-suppressor gene in a patient sample that can be correlated with a copy number gain of at least one metastasis-suppressor gene can be associated with a good prognosis. Low expression of the at least one metastasis-suppressor gene in a patient sample that can be correlated with a copy number loss of at least one metastasis-suppressor gene can be associated with a poor prognosis.

Poor prognosis can refer to any negative clinical outcome, such as, but not limited to, an increased risk of metastatic relapse, a decrease in likelihood of survival, a decrease in the time of survival (e.g., less than 5 years, or less than one year), an increase in the severity of disease, a decrease in response to therapy, an increase in tumor recurrence, or the like. A poor prognosis can indicate that a patient is a candidate for chemotherapy.

Good prognosis can refer to any positive clinical outcome, such as, but not limited to, a decreased risk of metastatic relapse, an increase in likelihood of survival, an increase in time of survival (e.g., more than 5 years, or more than one year), a decrease in the severity of disease, an increase in response to therapy, a decrease in tumor recurrence, or the like. A good prognosis can indicate that a patient is not in need of chemotherapy.

The patient can be a mammal, and is preferably human. The patient can have a non-metastatic primary tumor, or an early stage cancer. For example, the patient can have Dukes' A or B stage colorectal cancer, or an equivalent stage under another staging system.

The control can be any suitable control or threshold value against which to compare a level of an indicator of metastatic relapse in a biological sample from a patient. The control or control sample can be a non-tumor tissue or a reference value. For example, the reference value can be derived from average expression values obtained from a group of healthy control subjects or non-tumor tissue from a group of CRC patients.

The biological sample can be a cell or population of cells or a quantity of tissue or fluid from a patient. Often, a biological sample will contain cells from the patient, but the term can also refer to non-cellular biological material, such as non-cellular fractions of blood, saliva, or urine. Preferred biological samples can include tissue biopsies (from the primary cancer either frozen section or obtained from formalin-fixed paraffin-embedded tissue sections), scrapes (e.g. buccal scrapes), whole blood, plasma, serum, urine, saliva, cell culture, or cerebrospinal fluid.

Specific sequences for the genes and proteins referred to herein could be readily identified by a skilled person, for example, in gene and nucleic acid sequence databases available at the web site of the National Centre for Biotechnology Information (NCBI) web site, including GenBank. The metastasis-inducing genes and the metastasis-suppressor genes can encompass nucleic acid sequences or partial sequences encoding proteins having a polypeptide sequence corresponding to naturally occurring sequences, as well as variant or homologous polypeptide sequences, fragments, analogies and derivatives having an activity at least substantially identical to a wild-type protein. Likewise, the proteins referred to herein are intended to encompass proteins and polypeptides having amino acid sequences corresponding to naturally occurring sequences, as well as variant or homologous polypeptide sequences, fragments and derivatives having an activity at least substantially identical to a wild-type protein.

Detecting a level of at least one indicator of metastatic potential can include measuring a copy number of the metastasis-inducing gene and/or metastasis-suppressor gene.

The copy number in a sample can be determined using techniques known in the art, e.g., microarray, quantitative PCR, fluorescent in situ hybridization, comparative genomic hybridization (CGH), or array comparative genomic hybridization. For example, genomic DNA can be amplified, such as by PCR, to detect the presence or absence of gene deletions of one or more of metastasis-suppressor genes (ZNF366, C5orf48, CSMD1, NAT1, NAT2, SPAG11A, ADRA1A, EPHX2, ZNF703, BRF2, RAB11FIP1, ADRB3, WDR5, DIO3, ONECUT1, C20orf202, SIRPD, ADRA1D, MCM8, LOC339593, GP1BB, CABIN1, TOP1P2, ZNRF3, KIAA1656, APOBEC3D, CACNA1I, FAM83F, and/or PCDHGA11) and/or the presence or absence of gene amplification of one or more metastasis-inducing genes (CDC42BPA, VLDLR, GLIS3, MPDZ, SMU1, ANXA2P2, SCEL, DUSP14, USP32, PITPNC1, SEMG1, DOK5, and/or ING1).

A microarray can be characterized by the inclusion of genomic regions wherein a variation in a genomic region is consistent with one or more of the copy number variations listed in Table 1. Thus, the microarray can include a substrate with a plurality of distinct genomic regions arrayed thereon. Any substrate useful in forming diagnostic arrays may be used according to the present invention. For example, glass substrates, such as glass slides, may be used. Other non-limiting examples of useful substrates include silicon-based substrates, metal incorporating substrates (e.g., gold and metal oxides, such as titanium dioxide), gels, and polymeric materials. Useful substrates may be functionalized, such as to provide a specific charge, charge density, or functional group present at the substrate surface for immobilization of materials (e.g., oligonucleotides) to the substrate.

Detecting a level of the indicator of metastatic potential can include determining a level of gene expression products of the metastasis-inducing gene and/or metastasis-suppressor gene. The gene expression products can be mRNA and/or protein. The mRNA/protein expression can be determined by known methods, e.g., in situ hybridization, reverse transcription PCR, immunohistochemistry. For example, mRNA can be quantified by isolating RNA from a biological sample (e.g., solid tumor) from a patient. General methods for mRNA extraction are well known in the art. For example, RNA isolation can be performed using a purification kit, buffer set and protease from commercial manufacturers, such as QIAGEN®, according to the manufacturer's instructions. Total RNA from cells in culture (such as those obtained from a subject) can be isolated using QIAGEN® RNeasy mini-columns Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods for quantifying mRNA are well known in the art. In some examples, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Where the gene expression product to be measured is a protein, the protein can be indirectly assessed by activity levels of the protein. However, it is preferred that the level of the protein be assessed directly. For example, suitable methods for assessing protein levels include immunohistochemistry (e.g., immunostaining, immunofluorescence), western blotting, and solid phase methods such as ELISA (enzyme-linked immunoabsorbant assay). Using immunohistochemical techniques, an assessment of protein level can be made by determining the proportion of cells showing labelling and/or the intensity of the labelling (e.g., staining or fluorescence).

Also provided are methods for treating a patient diagnosed with early stage colorectal cancer (CRC). The method of treatment can include identifying patients at risk of metastatic relapse from CRC and administering cancer treatment to reduce or prevent metastasis to those patients. The cancer treatment can be, for example, chemotherapy.

Also provided is a kit for detecting one or more indicators of metastasis in order to determine treatment for a patient diagnosed with CRC. The kit can include a panel for detecting at least one indicator of metastasis or a gene expression product of the at least one indicator of metastasis, and instructions for use. The panel is a genetic panel that simultaneously evaluates multiple genes, as opposed to sequential testing of individual genes. This includes panels performed by next generation sequencing, massive parallel sequencing, microarray testing, or any other technique for simultaneously testing multiple genes. For detecting at least one indicator of metastasis or an mRNA gene expression product of the at least one indicator of metastasis, the panel can include complementary nucleic acid molecules that specifically hybridize to the nucleic acid molecules under conditions appropriate to the specific assay, which are widely known. The nucleic acids to be detected or the complementary nucleic acids (termed "probes") may be labeled, for example, fluorescently or with a radioactive isotope. Synthetic probes may also be generated and encompass non-natural or modified nucleotides, such as locked nucleic acid (LNA) or peptide nucleic acid (PNA), for example. Suitable assays to detect nucleic acids may include (but are not limited to) microarrays (including cDNA- or oligonucleotide-based, for example), RNA hybridization (Northern blot, slot blot, or dot blot, for example), PCR (quantitative or real time RT-PCR, for example), or genotyping methods, including SNP genotyping methods (e.g. restriction fragment length polymorphism (RFLP), sequencing, primer extension, 5'-nuclease, or oligonucleotide ligase-based assays, for example), etc. For detecting protein gene expression products of the at least one indicator of metastasis, the panel can include antibodies (monoclonal or polyclonal), fragments thereof, or antigen-binding polypeptides capable of specifically binding to the intended target proteins. Suitable antibodies may, in some instances, be purchased or may be generated through known methods. Suitable assays for detecting the protein may encompass immunohistochemistry methods or immunoassays, such as an enzyme linked immunosorbent assay (ELISA).

The following examples are provided by way of illustration.

EXAMPLES

A cohort of 116 patients with CRC was tested for metastatic relapse. The clinicopathological characteristics of the cohort are shown in Table 2.

TABLE 2

| Patients' Characteristics | Number (Percentage) |
|---|---|
| Sex | |
| Male | 57 (49) |
| Female | 59 (51) |
| Localization | |
| Right | 28 (24.1) |
| Left | 47 (40.5) |
| Rectum | 23 (19.8) |
| Colon unspecified | 18 (15.5) |
| T-stage | |
| T-3 | 62 (53.4) |
| T-4 | 25 (21.6) |
| Unknown | 29 (25.0) |
| Differentiation | |
| Well | 13 (11.2) |
| Moderate | 84 (72.4) |
| Poor | 11 (9.5) |
| Unknown | 8 (6.9) |
| Dukes' stage | |
| Dukes' B | 96 (82.8) |
| Dukes' C | 18 (15.5) |
| Dukes' D | 2 (1.7) |
| Follow-up Relapsed | |
| Metastasis | 11 (9.5) |
| Local | 13 (11.2) |
| Disease Free | 73 (62.9) |
| Unknown | 19 (16.4) |
| MSI Status | |
| MSI | 18 (15.5) |
| MSS | 90 (77.6) |
| Unknown | 8 (6.9) |
| Nationality | |
| West Asian | 37 (31.9) |
| European | 79 (68.1) |

For statistical analysis, log 2 ratio values of test vs. control were imported to Nexus Copy Number software (Biodiscovery, El Segundo, Calif.). Quality values ranged between 0.05-0.4. To minimize false positive calls and random CNV variations, Fast Adaptive State Segmentation Technique (FASST2) with a stringent significance threshold of 5.0E-6 was used to determine copy number aberrations. The systematic method termed Genomic Identification of Significant Targets in Cancer (GISTIC) was used to identify biologically significant copy number aberrations in the samples.

Genomic aberrations (e.g., copy number gain or loss) were present at a particular location on the genome in a number of samples and lacking in others. FIG. 1 identifies genomic loci associated with metastasis. The exact chromosomal positions of these regions are shown in Table 1. These regions include about 1000 genes. Each column in FIG. 1 represents a chromosome, with darker bars indicating a copy number gain and lighter bars indicating a copy number loss. To determine genomic loci associated with metastasis in CRC, two statistical approaches were used. In the first approach, using supervised clustering, copy number aberrations in CRC patients who stayed disease-free (n=73) were compared with those who relapsed with metastasis (n=11). The genomic copy number aberrations in cancers significantly associated with metastatic phenotype were mapped to the corresponding chromosomes (identified as "I" in FIG. 1). Then, in the second approach, using Predictive Power Analysis (Nexus), correlations were made between genomic aberrations and survival The copy number aberrations associated with reduced, disease-free survival were mapped to the corresponding chromosomes (identified as "II" in FIG. 1). Patients who relapsed with metastasis were grouped in the "In" group. Patients who were metastasis-free were grouped in the "Out" group. Genomic loci of the two approaches (I and II) were compared and copy number aberrations that were common to both were determined to be loci involved in or associated with metastatic relapse. These genomic loci associated with metastasis are shown in the top panel of FIG. 1.

The expression and survival predictive power or potential of each of the 1000 genes were tested on a separate and independent cohort including 1604 patients with CRC. Samples from all of the 1820 patients with CRC were profiled using the Affymetrix U133A or U133Plus2 platforms. Micorarray gene expression data was downloaded from Array Express from European Bioinformatics Institute (EBI) and Gene Expression Omnibus from NCBI. Each gene expression profile (at the mRNA level) was assessed in terms of its influence on overall survival and disease-free survival, using Cox regression and Kaplan-Meier survival log-rank test. Also assessed for each gene was expression of each gene and clinicopathological association with tumor grade, CRC stage, microsatellite instability, and Epithelial to Mesenchymal Transition (EMT) using Spearman's Rho analysis. The expression of each of the genes in CRC was further compared to that of a normal colon. 42 genes (listed in Table 1) were identified that influence survival in CRC. Data relating to ANXA2P2, an exemplary metastasis-inducing gene that is located on chromosome 9p13.3, is provided in FIGS. 2-10. Data relating to NAT1, an exemplary metastasis-suppressor gene that is located on chromosome 8p22, is provided in FIGS. 11-19.

FIG. 2 reflects the correlation between ANXA2P2 gene expression and clinicopathological association with EMT (where Rho is 0.1721 and p value is 1.84e-13).

FIG. 3 reflects the correlation between ANXA2P2 gene expression and clinicopathological association with tumor grade. The mean expression values were 10.76, 10.67, and 10.80, for Grades 1, 2, and 3, respectively. The lower 95% Confidence Interval (CI) for Grade 1 was 10.62 and the upper 95% CI was 10.90. The lower 95% CI for Grade 2 was 10.62 and the upper 95% CI was 10.72. The lower 95% CI for Grade 3 was 10.69 and the upper 95% CI was 10.90.

FIG. 4 reflects the correlation between ANXA2P2 gene expression and clinicopathological association with microsatellite instability. The mean expression values were 10.63, and 10.87, for microsatellite stability (MSS) and microsatellite instability (MSI), respectively. The lower 95% Confidence interval (CI) for MSS was 10.59 and the upper 95% CI was 10.67. The lower 95% CI for MSI was 10.82 and the upper 95% CI was 10.92.

FIG. 5 reflects the correlation between ANXA2P2 gene expression and clinicopathological association with CRC stage. The mean expression values were 10.57, 10.73, 10.72, and 10.72 for stage I, stage II, stage III, and stage IV, respectively. The lower 95% CI for stage I was 10.44 and the upper 95% CI was 10.69. The lower 95% CI for stage II was 10.66 and the upper 95% CI was 10.79. The lower 95% CI for stage III was 10.64 and the upper 95% CI was 10.80. The lower 95% CI for stage IV was 10.62 and the upper 95% CI was 10.83.

FIG. 6 reflects the correlation between ANXA2P2 gene expression and clinicopathological association with overall (disease specific) survival (Kaplan-Meier survival log-rank test), where n=514. The hazard ratio (HR) was 1.5886 (1.2401-2.0354). The p value was 0.0003. The median survival percentage associated with ANXA2P2 high expression was 55.92. The median survival percentage associated with ANXA2P2 low expression was 67.82. The 5-year survival percentage associated with ANXA2P2 high expression was 42.53. The 5-year survival percentage associated with ANXA2P2 low expression was 57.09. The 8.5-year survival percentage associated with ANXA2P2 high expression was 19.54. The 8.5-year survival percentage associated with ANXA2P2 low expression was 30.07.

FIG. 7 reflects the correlation between ANXA2P2 gene expression and clinicopathological association with disease-free survival (Kaplan-Meier survival log-rank test) where n=457. The hazard ratio (HR) was 1.7391 (1.2650-2.3912). The p value was 0.0007. The median survival percentage associated with ANXA2P2 high expression was 93.66. The median survival percentage associated with ANXA2P2 low expression was undefined. The 5-year survival percentage associated with ANXA2P2 high expression was 54.81. The 5-year survival percentage associated with ANXA2P2 low expression was 72.16. The 8.5-year survival percentage associated with ANXA2P2 high expression was 49.83. The 8.5-year survival percentage associated with ANXA2P2 low expression was 66.3.

FIG. 8 reflects the correlation between ANXA2P2 gene expression and clinicopathological association with normal colon vs. CRC tumor. The mean expression values were 10.6, and 10.72, for normal colon and CRC tumor, respectively. The lower 95% CI for normal colon was 101.54 and the upper 95% CI was 10.66. The lower 95% CI for CRC tumor was 10.70 and the upper 95% CI was 10.74.

FIG. 9 reflects the correlation between ANXA2P2 gene expression and clinicopathological association with overall (disease specific) survival (Kaplan-Meier survival log-rank test), where n=257. The hazard ratio (HR) was 1.4575 (1.0348-2.053). The p value was 0.0311. The median survival percentage associated with ANXA2P2 high expression was 55.92. The median survival percentage associated with ANXA2P2 low expression was 61.4. The 5-year survival percentage associated with ANXA2P2 high expression was 41.29. The 5-year survival percentage associated with ANXA2P2 low expression was 51.21. The 8.5-year survival percentage associated with ANXA2P2 high expression was 17.76. The 8.5-year survival percentage associated with ANXA2P2 low expression was 34.53.

FIG. 10 reflects the correlation between ANXA2P2 gene expression and clinicopathological association with disease-free survival (Kaplan-Meier survival log-rank test) where n=228. The hazard ratio (HR) was 1.4789 (0.9569-2.31).

The p value was 0.0776. The median survival percentage associated with ANXA2P2 high expression was 93.66. The median survival percentage associated with ANXA2P2 low expression was undefined. The 5-year survival percentage associated with ANXA2P2 high expression was 54.89. The 5-year survival percentage associated with ANXA2P2 low expression was 68.88. The 8.5-year survival percentage associated with ANXA2P2 high expression was 43.91. The 8.5-year survival percentage associated with ANXA2P2 low expression was 58.44.

Data obtained for Nat1, a metastasis-suppressor gene located in a region of chromosome 8p22, is provided in FIGS. 11-19.

FIG. 11 reflects the correlation between Nat1 gene expression and clinicopathological association with EMT (where Rho is 0.1939 and p value is 9.65e-17).

FIG. 12 reflects the correlation between Nat1 gene expression and clinicopathological association with tumor grade. The mean expression values were 8.456, 8.378, and 8.475, for Grades 1, 2, and 3, respectively. The lower 95% Confidence Interval (CI) for Grade 1 was 8.130 and the upper 95% CI was 8.783. The lower 95% CI for Grade 2 was 8.276 and the upper 95% CI was 8.480. The lower 95% CI for Grade 3 was 8.289 and the upper 95% CI was 8.661.

FIG. 13 reflects the correlation between NAT1 gene expression and clinicopathological association with microsatellite instability. The mean expression values were 8.280, and 8.564, for microsatellite stability (MSS) and microsatellite instability (MSI), respectively. The lower 95% CI for MSS was 8.198 and the upper 95% CI was 8.362. The lower 95% CI for MSI was 8.465 and the upper 95% CI was 8.663.

Figure 14:
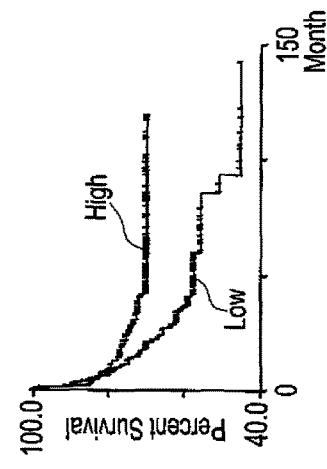
FIG. 14 is a graph showing the correlation between NAT1 gene expression and clinicopathological association with CRC stage.

FIG. 14 reflects the correlation between NAT1 gene expression and clinicopathological association with CRC stage. The mean expression values were 8.700, 8.432, 8.291, and 8.319 for stage I, stage II, stage III, and stage IV, respectively. The lower 95% CI for stage I was 8.418 and the upper 95% CI was 8.983. The lower 95% CI for stage II was 8.314 and the upper 95% CI was 8.550. The lower 95% CI for stage III was 8.140 and the upper 95% CI was 8.442. The lower 95% CI for stage IV was 8.091 and the upper 95% CI was 8.547.

Figure 15:
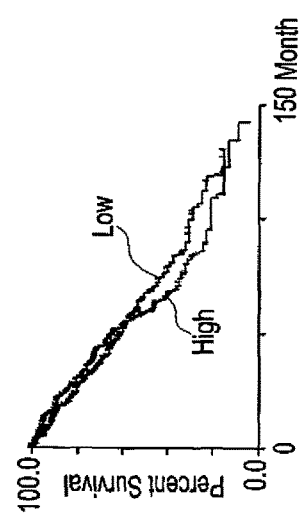
FIG. 15 is a graph showing the correlation between NAT1 gene expression and clinicopathological association with overall (disease specific) survival (Kaplan-Meier survival log-rank test).

FIG. 15 reflects the correlation between NAT1 gene expression and clinicopathological association with overall (disease specific) survival (Kaplan-Meier survival log-rank test), where n=514. The hazard ratio (HR) was 0.9373 (0.7327-1.199). The p value was 0.6063. The median survival percentage associated with NAT1 high expression was 59.07. The median survival percentage associated with NAT1 low expression was 67.82. The 5-year survival percentage associated with NAT1 high expression was 46.81. The 5-year survival percentage associated with NAT1 low expression was 53.22. The 8.5-year survival percentage associated with NAT1 high expression was 20.75. The 8.5-year survival percentage associated with NAT1 low expression was 29.02.

Figure 16:
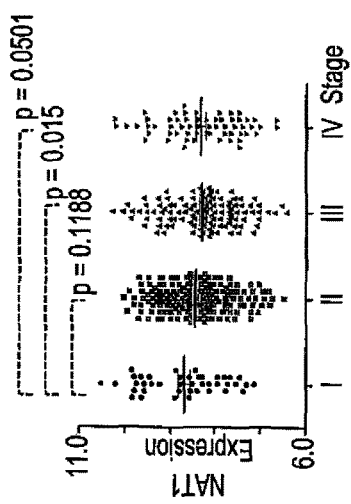
FIG. 16 is a graph showing the correlation between NAT1 gene expression and clinicopathological association with disease-free survival (Kaplan-Meier survival log-rank test).

FIG. 16 reflects the correlation between NAT1 gene expression and clinicopathological association with disease-free survival (Kaplan-Meier survival log-rank test) where n=457. The hazard ratio (HR) was 1.505 (1.095-2.068). The p value was 0.0117. The median survival percentage associated with NAT1 low expression was 93.66. The 5-year survival percentage associated with NAT1 high expression was 70.05. The 5-year survival percentage associated with NAT1 low expression was 57.34. The 8.5-year survival percentage associated with NAT1 high expression was 70.05. The 8.5-year survival percentage associated with NAT1 low expression was 45.11.

Figure 17:
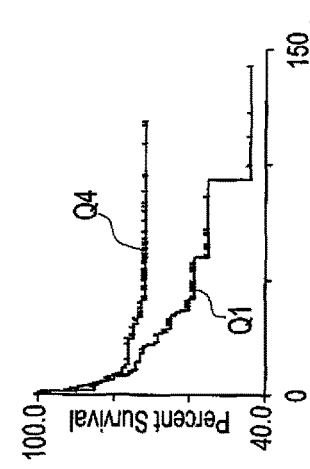
FIG. 17 is a graph showing the correlation between NAT1 gene expression and clinicopathological association with normal colon vs. CRC tumor.

FIG. 17 reflects the correlation between NAT1 gene expression and clinicopathological association with normal colon vs. CRC tumor. The mean expression values were 8.797, and 8.367, for normal colon and CRC tumor, respectively. The lower 95% CI for normal colon was 8.671 and the upper 95% CI was 8.923. The lower 95% CI for CRC tumor was 8.329 and the upper 95% CI was 8.404.

Figure 18:
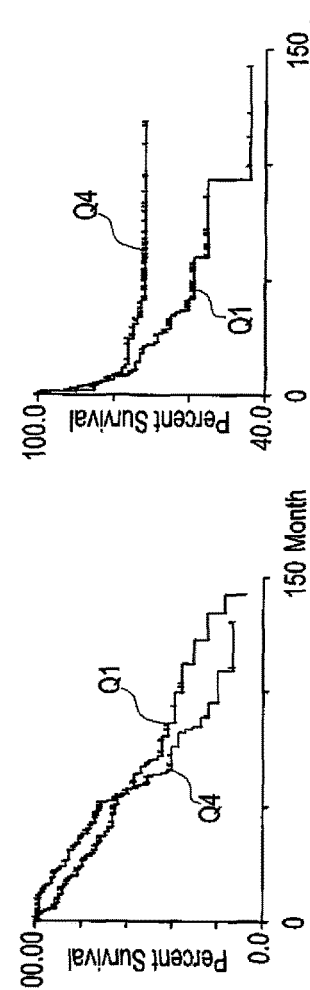
FIG. 18 is a graph showing the correlation between NAT1 gene expression and clinicopathological association with overall (disease specific) survival (Kaplan-Meier survival log-rank test).

FIG. 18 reflects the correlation between NAT1 gene expression and clinicopathological association with overall (disease specific) survival (Kaplan-Meier survival log-rank test), where n=257. The hazard ratio (HR) was 0.9275 (0.6431-1.338). The p value was 0.6872. The median survival percentage associated with NAT1 Q1 was 70.45. The median survival percentage associated with NAT1 Q4 was 63.25. The 5-year survival percentage associated with NAT1 Q1 was 57.04. The 5-year survival percentage associated with NAT1 Q4 was 50.65. The 8.5-year survival percentage associated with NAT1 Q1 was 35.51. The 8.5-year survival percentage associated with NAT1 Q4 was 19.24.

Figure 19:
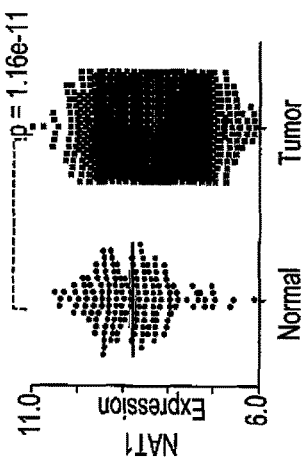
FIG. 19 is a graph showing the correlation between NAT1 gene expression and clinicopathological association with disease-free survival (Kaplan-Meier survival log-rank test).

FIG. 19 reflects the correlation between NAT1 gene expression and clinicopathological association with disease-free survival (Kaplan-Meier survival log-rank test) where n=228. The hazard ratio (HR) was 1.52 (0.9592-2.407). The p value was 0.0747. The median survival percentage associated with NAT1 Q1 was 93.66. The 5-year survival percentage associated with NAT1 Q1 was 58.7. The 5-year survival percentage associated with NAT1 Q4 was 71.7. The 8.5-year survival percentage associated with NAT1 Q1 was 44.2. The 8.5-year survival percentage associated with NAT1 Q4 was 71.7.

Data generated for each of the genes are summarized in the Tables 3-12. Tables 3, 5, 7, 9, and 11 include data relating to the metastasis-inducing genes. Tables 4, 6, 8, 10, and 12 include data relating to the metastasis-suppressor genes. As noted, some of the data reflected in Tables 3-12, e.g., correlating expression level with tumor grade or clinical stage, was obtained using the Mann-Whitney U-test.

TABLE 3

CNV and Correlation of Expression with EMT, Disease Specific Survival (DSS), and Disease Free Survival (DFS)

| Gene | % CNV | CNV Event | On Affy U133P2? | EMT Correl. | DSS | DFS |
| --- | --- | --- | --- | --- | --- | --- |
| ADRA1A | 0.420711 | Loss | 1 | — | — | High Expn/Good Prog |
| ADRA1D | 1.155894 | Loss | 1 | — | High Expn/Good Prog | — |
| ADRB3 | 0 | Loss | 1 | — | High Expn/Good Prog | — |
| APOBEC3D | 0 | Loss | 1 | — | — | High Expn/Good Prog |
| BRF2 | 0 | Loss | 1 | — | High Expn/Good Prog | — |
| C20orf202 | 0.890097 | Loss | 1 | — | High Expn/Good Prog | — |
| C5orf48 | 0 | Loss | 1 | — | — | High Expn/Good Prog |
| CABIN1 | 4.022346 | Loss | 1 | — | High Expn/Good Prog | — |

TABLE 3-continued

CNV and Correlation of Expression with EMT, Disease Specific Survival (DSS), and Disease Free Survival (DFS)

| Gene | % CNV | CNV Event | On Affy U133P2? | EMT Correl. | DSS | DFS |
|---|---|---|---|---|---|---|
| CACNA1I | 0 | Loss | 1 | — | High Expn/Good Prog | — |
| CSMD1 | 0 | Loss | 1 | — | — | High Expn/Good Prog |
| DIO3 | 1.760261 | Loss | 1 | — | High Expn/Good Prog | — |
| EPHX2 | 0.420711 | Loss | 1 | Negative | — | High Expn/Good Prog |
| FAM83F | 0 | Loss | 1 | Negative | — | High Expn/Good Prog |
| GP1BB | 0 | Loss | 1 | — | High Expn/Good Prog | — |
| KIAA1656 | 0 | Loss | 1 | — | High Expn/Good Prog | High Expn/Good Prog |
| LOC339593 | 0.174694 | Loss | 1 | — | — | High Expn/Good Prog |
| MCM8 | 0 | Loss | 1 | — | — | High Expn/Good Prog |
| NAT1 | 0 | Loss | 1 | Negative | — | High Expn/Good Prog |
| NAT2 | 0 | Loss | 1 | Negative | — | High Expn/Good Prog |
| ONECUT1 | 0 | Loss | 1 | — | High Expn/Good Prog | — |
| PCDHGA11 | 0 | Loss | 1 | — | High Expn/Good Prog | — |
| RAB11FIP1 | 0 | Loss | 1 | Negative | High Expn/Good Prog | — |
| SPAG11A | 68.65734 | Loss | 1 | — | High Expn/Good Prog | — |
| SIRPD | 0.890097 | Loss | 1 | — | High Expn/Good Prog | — |
| TOP1P2 | 0 | Loss | 1 | — | High Expn/Good Prog | — |
| WDR5 | 0 | Loss | 1 | Negative | — | High Expn/Good Prog |
| ZNF366 | 0.075726 | Loss | 1 | — | High Expn/Good Prog | — |
| ZNF703 | 0 | Loss | 1 | Negative | High Expn/Good Prog | — |
| ZNRF3 | 0 | Loss | 1 | Negative | — | High Expn/Good Prog |

TABLE 4

CNV and Correlation of Expression with EMT, Disease Specific Survival (DSS), and Disease Free Survival (DFS)

| Gene | % CNV Overlap | CNV Event | Kaplan Meier verification | EMT correlation | Cox's DSS | Cox's DFS |
|---|---|---|---|---|---|---|
| MPDZ | 0 | Gain | Yes/DFS | Positive | — | High Expn/Poor Prog |
| DUSP14 | 0.705287 | Gain | Yes/DSS | Positive | High Expn/Poor Prog | High Expn/Poor Prog |
| SCEL | 0 | Gain | Yes/DSS & DFS | — | — | High Expn/Poor Prog |
| ANXA2P2 | 0 | Gain | Yes/DSS & DFS | — | High Expn/Poor Prog | High Expn/Poor Prog |
| GLIS3 | 1.246986 | Gain | Yes/DFS | Positive | — | High Expn/Poor Prog |
| DOK5 | 0.570217 | Gain | Yes/DSS | Positive | — | High Expn/Poor Prog |
| VLDLR | 0.138053 | Gain | Yes/DFS | — | — | High Expn/Poor Prog |
| CDC42BPA | 0 | Gain | Yes/DFS Q4 | — | — | High Expn/Poor Prog |
| USP32 | 0 | Gain | Yes/DSS | Positive | — | High Expn/Poor Prog |
| PITPNC1 | 0 | Gain | DSS | — | High Expn/Poor Prog | High Expn/Poor Prog |
| SEMG1 | 0 | Gain | DFS | — | High Expn/Poor Prog | — |
| SMU1 | 0.734073 | Gain | DSS | — | High Expn/Poor Prog | — |
| ING1 | 0 | Gain | DSS Q4 | — | High Expn/Poor Prog | — |

TABLE 5

Expression Diff. in Tumor vs. Normal, CRC Grade, CRC Stage, & MSS vs. MSI/Spearman's Rho and P value (EMT)

| Gene | Tumor vs Normal | Grade | Stage | MSS vs MSI | Spear.EMT. Corr.Rho | Spear.EMT. Corr.pv |
|---|---|---|---|---|---|---|
| ADRA1A | Sig. Diff. | — | — | Sig. Diff. | −0.11554 | 1.14E−05 |
| ADRA1D | — | — | Sig. Diff. | — | −0.10702 | 4.83E−05 |
| ADRB3 | Sig. Diff. | Sig. Diff. | Sig. Diff. | Sig. Diff. | −0.12734 | 1.29E−06 |
| APOBEC3D | Sig. Diff. | — | — | — | −0.04603 | 8.12E−02 |
| BRF2 | — | — | — | Sig. Diff. | 0.043368 | 1.00E−01 |
| C20orf202 | — | — | — | Sig. Diff. | −0.08187 | 1.90E−03 |
| C5orf48 | Sig. Diff. | — | — | Sig. Diff. | −0.12857 | 1.02E−06 |
| CABIN1 | — | — | — | Sig. Diff. | 0.006294 | 8.12E−01 |
| CACNA1I | Sig. Diff. | — | Sig. Diff. | Sig. Diff. | −0.18416 | 2.02E−12 |
| CSMD1 | — | — | Sig. Diff. | — | −0.1708 | 7.28E−11 |
| DIO3 | Sig. Diff. | — | Sig. Diff. | Sig. Diff. | −0.12678 | 1.44E−06 |
| EPHX2 | Sig. Diff. | — | — | — | −0.31109 | 1.36E−33 |
| FAM83F | Sig. Diff. | — | — | Sig. Diff. | −0.38216 | 3.78E−51 |

TABLE 5-continued

Expression Diff. in Tumor vs. Normal, CRC Grade, CRC Stage, & MSS vs. MSI/Spearman's Rho and P value (EMT)

| Gene | Tumor vs Normal | Grade | Stage | MSS vs MSI | Spear.EMT. Corr.Rho | Spear.EMT. Corr.pv |
|---|---|---|---|---|---|---|
| GP1BB | Sig. Diff | Sig. Diff. | — | Sig. Diff. | −0.11784 | 7.56E−06 |
| KIAA1656 | Sig. Diff. | Sig. Diff. | — | Sig. Diff. | −0.11734 | 8.27E−06 |
| LOC339593 | — | — | Sig. Diff. | — | −0.11113 | 2.44E−05 |
| MCM8 | Sig. Diff. | — | — | Sig. Diff. | −0.12744 | 1.27E−06 |
| NAT1 | Sig. Diff. | — | Sig. Diff. | Sig. Diff. | −0.22961 | 1.24E−18 |
| NAT2 | Sig. Diff. | Sig. Diff. | Sig. Diff. | Sig. Diff. | −0.36097 | 1.96E−45 |
| ONECUT1 | Sig. Diff. | — | — | Sig. Diff. | −0.05085 | 5.40E−02 |
| PCDHGA11 | — | — | — | — | −0.15348 | 5.05E−09 |
| RAB11FIP1 | Sig. Diff. | — | Sig. Diff. | — | −0.30085 | 2.00E−31 |
| SPAG11A | — | — | Sig. Diff. | — | −0.0079 | 7.65E−01 |
| SIRPD | — | — | Sig. Diff. | Sig. Diff. | 0.055333 | 3.60E−02 |
| TOP1P2 | — | — | — | — | −0.04795 | 6.93E−02 |
| WDR5 | Sig. Diff. | — | — | Sig. Diff. | −0.30379 | 4.86E−32 |
| ZNF366 | — | — | Sig. Diff. | — | −0.06771 | 1.03E−02 |
| ZNF703 | Sig. Diff. | Sig. Diff. | — | Sig. Diff. | −0.32778 | 2.58E−37 |
| ZNRF3 | Sig. Diff. | Sig. Diff. | Sig. Diff. | Sig. Diff. | −0.24291 | 9.91E−21 |

TABLE 6

Expression Diff. in Tumor vs. Normal, CRC Grade, CRC Stage, & MSS vs. MSI/Spearman's Rho and P value (EMT)

| Gene | Tumor v. Normal | Grade | Stage | MSS vs MSI | Spear.EMT. Corr.Rho | Spear.EMT. Corr.pv |
|---|---|---|---|---|---|---|
| MPDZ | Sig. Diff. | Sig. Diff. | Sig. Diff. | — | 0.683395 | 3.43E−198 |
| DUSP14 | Sig. Diff. | Sig. Diff. | Sig. Diff. | Sig. Diff. | 0.316919 | 7.25E−35 |
| SCEL | Sig. Diff. | Sig. Diff. | Sig. Diff. | — | 0.062208 | 1.84E−02 |
| ANXA2P2 | Sig. Diff. | Sig. Diff. | Sig. Diff. | Sig. Diff. | 0.016965 | 5.21E−01 |
| GLIS3 | — | Sig. Diff. | Sig. Diff. | — | 0.308117 | 5.90E−33 |
| DOK5 | — | Sig. Diff. | Sig. Diff. | — | 0.656223 | 1.33E−177 |
| VLDLR | Sig. Diff. | — | Sig. Diff. | Sig. Diff. | 0.107559 | 4.42E−05 |
| CDC42BPA | Sig. Diff. | — | — | — | 0.006847 | 0.795453 |
| USP32 | — | — | — | Sig. Diff. | 0.215219 | 1.65E−16 |
| PITPNC1 | Sig. Diff. | — | — | Sig. Diff. | 0.000786 | 9.76E−01 |
| SEMG1 | — | — | — | Sig. Diff. | −0.07814 | 3.05E−03 |
| SMU1 | Sig. Diff. | — | — | Sig. Diff. | −0.02528 | 0.338419 |
| ING1 | Sig. Diff. | — | Sig. Diff. | Sig. Diff. | −0.04653 | 7.80E−02 |

TABLE 7

P values (Mann-Whitney) Correlating Gene Expression with Differences in Tumor Grade

| Gene | Grade 1 vs. Grade 2. MWpv | Grade 1 vs. Grade3. MW. pv | Grade 2 vs. Grade3. MW. pv |
|---|---|---|---|
| ADRA1A | 0.200865 | 0.909476 | 0.07734 |
| ADRA1D | 0.102804 | 0.275505 | 0.477323 |
| ADRB3 | 0.166421 | 0.025572 | 0.084262 |
| APOBEC3D | 0.833025 | 0.705971 | 0.457078 |
| BRF2 | 0.108288 | 0.257709 | 0.640776 |
| C20orf202 | 0.411843 | 0.784154 | 0.485192 |
| C5orf48 | 0.555174 | 0.616151 | 0.112187 |
| CABIN1 | 0.512398 | 0.897197 | 0.351707 |
| CACNA1I | 0.230195 | 0.66045 | 0.480946 |
| CSMD1 | 0.433949 | 0.080664 | 0.08836 |
| DIO3 | 0.180268 | 0.121035 | 0.521137 |
| EPHX2 | 0.951485 | 0.848353 | 0.823836 |
| FAM83F | 0.593739 | 0.756492 | 0.192038 |
| GP1BB | 0.025659 | 0.016719 | 0.390149 |
| KIAA1656 | 0.022059 | 0.354918 | 0.33879 |
| LOC339593 | 0.885246 | 0.702133 | 0.753526 |
| MCM8 | 0.199375 | 0.590931 | 0.426505 |
| NAT1 | 0.670187 | 0.538551 | 0.112849 |
| NAT2 | 0.428978 | 0.29412 | 0.001922 |
| ONECUT1 | 0.058524 | 0.201768 | 0.590868 |
| PCDHGA11 | 0.113676 | 0.118576 | 0.620738 |
| RAB11FIP1 | 0.53823 | 0.26208 | 0.417514 |
| SPAG11A | 0.067325 | 0.14933 | 0.754265 |
| SIRPD | 0.847406 | 0.72139 | 0.775775 |
| TOP1P2 | 0.219921 | 0.872714 | 0.176931 |
| WDR5 | 0.562789 | 0.491856 | 0.727828 |
| ZNF366 | 0.108287 | 0.545399 | 0.392835 |
| ZNF703 | 0.621442 | 0.069676 | 0.011174 |
| ZNRF3 | 0.93572 | 0.062085 | 0.006155 |

TABLE 8

P values (Mann-Whitney) Correlating Gene Expression with Differences in Tumor Grade

| Gene | Grade 1 vs. Grade 2. MWpv | Grade 1 vs. Grade3. MW. pv | Grade 2 vs. Grade3. MW. pv |
|---|---|---|---|
| MPDZ | 0.019342 | 0.29412 | 0.097428 |
| DUSP14 | 0.605543 | 0.062085 | 0.007799 |
| SCEL | 0.039522 | 0.333825 | 0.225055 |
| ANXA2P2 | 0.322648 | 0.344263 | 0.015006 |
| GLIS3 | 0.068606 | 0.017196 | 0.291099 |
| DOK5 | 0.000225 | 0.036341 | 0.163315 |
| VLDLR | 0.824203 | 0.608901 | 0.675231 |
| CDC42BPA | 0.480159 | 0.385258 | 0.564302 |
| USP32 | 0.420768 | 0.20917 | 0.383217 |
| PITPNC1 | 0.35331 | 0.129961 | 0.237943 |
| SEMG1 | 0.258852 | 0.566197 | 0.680923 |
| SMU1 | 0.154207 | 0.98763 | 0.068939 |
| ING1 | 0.311019 | 0.580271 | 0.644258 |

TABLE 9

P values (Mann-Whitney) Correlating Gene Expression with CRC stage progression

| Gene | St. I vs. St. II | St. I vs. St. III | St.I vs. St.IV | St. II vs St. III | St. II vs. St. IV | St. III vs. St. IV |
|---|---|---|---|---|---|---|
| ADRA1A | 0.385629 | 0.054778 | 0.066347 | 0.127172 | 0.251446 | 0.849241 |
| ADRA1D | 0.785608 | 0.620774 | 0.116326 | 0.807158 | 0.026466 | 0.047567 |
| ADRB3 | 0.10136 | 0.106675 | 0.002672 | 0.989223 | 0.015087 | 0.014459 |
| APOBEC3D | 0.712223 | 0.101441 | 0.153276 | 0.093201 | 0.193716 | 0.987492 |
| BRF2 | 0.613642 | 0.415448 | 0.779541 | 0.486063 | 0.255382 | 0.108503 |
| C20orf202 | 0.75567 | 0.462678 | 0.345101 | 0.526794 | 0.33763 | 0.677814 |
| C5orf48 | 0.318561 | 0.138558 | 0.279374 | 0.356343 | 0.767092 | 0.782308 |
| CABIN1 | 0.544609 | 0.586498 | 0.779541 | 0.963063 | 0.161186 | 0.183319 |
| CACNA1I | 0.072997 | 0.493167 | 0.028731 | 0.139647 | 0.367745 | 0.046696 |
| CSMD1 | 0.153858 | 0.042229 | 0.007777 | 0.311502 | 0.098403 | 0.448219 |
| DIO3 | 0.02618 | 0.082522 | 0.003979 | 0.582364 | 0.32418 | 0.171977 |
| EPHX2 | 0.065733 | 0.057956 | 0.18561 | 0.946155 | 0.631153 | 0.639529 |
| FAM83F | 0.8723 | 0.374491 | 0.226341 | 0.274343 | 0.125788 | 0.655018 |
| GP1BB | 0.275655 | 0.320917 | 0.050063 | 0.968447 | 0.092493 | 0.103424 |
| KIAA1656 | 0.052232 | 0.081441 | 0.01574 | 0.828146 | 0.229776 | 0.222879 |
| LOC339593 | 0.937582 | 0.21104 | 0.518774 | 0.028447 | 0.171109 | 0.771792 |
| MCM8 | 0.62673 | 0.473988 | 0.83094 | 0.69029 | 0.726134 | 0.506484 |
| NAT1 | 0.023528 | 0.00892 | 0.01309 | 0.251721 | 0.23828 | 0.682123 |
| NAT2 | 0.001433 | 0.000855 | 0.007777 | 0.495168 | 0.990289 | 0.725755 |
| ONECUT1 | 0.149155 | 0.208807 | 0.303232 | 0.859855 | 0.798256 | 0.943758 |
| PCDHGA11 | 0.645843 | 0.455222 | 0.170335 | 0.68461 | 0.156389 | 0.288172 |
| RAB11FIP1 | 0.461923 | 0.914349 | 0.118548 | 0.322231 | 0.120851 | 0.039813 |
| SPAG11A | 0.103964 | 0.117781 | 0.018376 | 0.908595 | 0.137917 | 0.123967 |
| SIRPD | 0.083448 | 0.052494 | 0.000976 | 0.425495 | 0.020228 | 0.103424 |
| TOP1P2 | 0.486096 | 0.181304 | 0.060926 | 0.280316 | 0.08465 | 0.389628 |
| WDR5 | 0.054005 | 0.071256 | 0.095858 | 0.693848 | 0.728164 | 0.890892 |
| ZNF366 | 0.675705 | 0.885161 | 0.095857 | 0.597676 | 0.079882 | 0.040961 |
| ZNF703 | 0.634052 | 0.356582 | 0.3801 | 0.288125 | 0.417887 | 0.866165 |
| ZNRF3 | 0.687798 | 0.354983 | 0.212116 | 0.064105 | 0.196514 | 0.00523 |

TABLE 10

P values (Mann-Whitney) Correlating Gene Expression with CRC stage progression

| Gene | St. I vs. St. II | St. I vs. St. III | St. I vs. St. IV | St. II vs. St. III | St. II vs. St. IV | St. III vs. St. IV |
|---|---|---|---|---|---|---|
| MPDZ | 0.045841 | 0.009583 | 0.001658 | 0.477648 | 0.038911 | 0.182032 |
| DUSP14 | 0.002751 | 0.011843 | 0.017458 | 0.556179 | 0.880672 | 0.752379 |
| SCEL | 0.020656 | 0.005734 | 0.04278 | 0.206618 | 0.860441 | 0.193857 |
| ANXA2P2 | 0.035557 | 0.058363 | 0.077578 | 0.997691 | 0.872143 | 0.886247 |
| GLIS3 | 0.045841 | 0.000171 | 0.101671 | 0.038591 | 0.615848 | 0.012062 |
| DOK5 | 0.07008 | 0.006356 | 0.057107 | 0.130821 | 0.803482 | 0.393965 |
| VLDLR | 0.029086 | 0.051751 | 0.005432 | 0.750194 | 0.171961 | 0.186565 |
| CDC42BPA | 0.277474 | 0.169559 | 0.124249 | 0.30737 | 0.178417 | 0.667804 |
| USP32 | 0.579347 | 0.244156 | 0.164499 | 0.521766 | 0.303395 | 0.685001 |
| PITPNC1 | 0.073659 | 0.157487 | 0.156026 | 0.482447 | 0.723091 | 0.889343 |
| SEMG1 | 0.953987 | 0.185351 | 0.182477 | 0.080427 | 0.055664 | 0.66923 |
| SMU1 | 0.754104 | 0.997548 | 0.245083 | 0.732698 | 0.28963 | 0.142163 |
| ING1 | 0.021112 | 0.007786 | 0.006191 | 0.377871 | 0.093281 | 0.449392 |

TABLE 11

Expn. Correlation with MSS v. MSI, DSS, DFS, &
Tumor (T) v. Normal (N)/Cox-regression for DSS & DFS

| Gene | MSS v. MSI-M.W.pv | DSS-Cox beta | DSS-Cox pv | DFS-Cox beta | DFS-Cox pv | T v. N-M.W.pv |
|---|---|---|---|---|---|---|
| ADRA1A | 4.65E−02 | −0.40185 | 0.152322 | −1.67582 | 0.001948 | 0.000607 |
| ADRA1D | 6.67E−02 | −0.5968 | 0.020507 | 0.066504 | 0.880385 | 4.21E−01 |
| ADRB3 | 0.018867 | −1.21809 | 0.002366 | −1.12818 | 0.086011 | 3.12E−02 |
| APOBEC3D | 0.538426 | −0.45803 | 0.248528 | −1.56085 | 0.022398 | 0.001437 |
| BRF2 | 6.13E−06 | −0.45526 | 0.02013 | 0.061887 | 0.851517 | 1.44E−01 |
| C20orf202 | 0.011137 | −0.80141 | 0.000481 | −0.19907 | 0.628292 | 5.24E−02 |
| C5orf48 | 4.67E−03 | −0.46611 | 0.175471 | −1.60127 | 0.011617 | 1.17E−04 |
| CABIN1 | 4.10E−08 | −0.47782 | 0.021018 | −0.51601 | 0.14935 | 8.48E−02 |
| CACNA1I | 0.032276 | −0.69524 | 0.00404 | −0.73386 | 0.082677 | 4.77E−05 |
| CSMD1 | 0.308815 | −0.01578 | 0.956357 | −1.30789 | 0.019485 | 7.95E−01 |
| DIO3 | 4.58E−05 | −0.32561 | 0.041777 | −0.00829 | 0.973719 | 1.86E−02 |
| EPHX2 | 2.40E−01 | 0.036582 | 0.614111 | −0.30515 | 0.009956 | 2.15E−25 |
| FAM83F | 0.047495 | −0.13746 | 0.287004 | −0.72925 | 0.00085 | 1.97E−02 |
| GP1BB | 4.17E−02 | −0.56827 | 0.000246 | −0.19289 | 0.495577 | 3.33E−04 |
| KIAA1656 | 1.37E−02 | −0.60241 | 0.01922 | −1.02118 | 0.032326 | 1.53E−04 |
| LOC339593 | 2.46E−01 | 0.29021 | 0.385267 | −1.12678 | 0.047789 | 8.75E−01 |
| MCM8 | 2.74E−02 | 0.043419 | 0.614947 | −0.31948 | 0.034203 | 1.27E−15 |
| NAT1 | 5.71E−06 | 0.028159 | 0.713606 | −0.36337 | 0.007197 | 2.62E−11 |
| NAT2 | 7.89E−03 | −0.09059 | 0.160865 | −0.30169 | 0.003804 | 1.86E−16 |
| ONECUT1 | 9.65E−03 | −0.66924 | 0.017955 | −0.51152 | 0.309992 | 4.04E−02 |
| PCDHGA11 | 7.69E−02 | −0.85799 | 0.013435 | −0.577 | 0.33928 | 0.926676 |
| RAB11FIP1 | 4.69E−01 | −0.38036 | 5.55E−05 | −0.02196 | 0.892186 | 5.70E−06 |
| SPAG11A | 3.67E−01 | −0.81665 | 0.001447 | −0.13298 | 0.763944 | 5.53E−01 |
| SIRPD | 3.25E−02 | −0.89166 | 0.014166 | −0.13392 | 0.821484 | 4.27E−01 |
| TOP1P2 | 2.12E−01 | −1.13965 | 0.005692 | 0.599602 | 0.328562 | 6.52E−01 |
| WDR5 | 1.09E−02 | −0.0007 | 0.995962 | −0.52505 | 0.024307 | 4.33E−10 |
| ZNF366 | 1.23E−01 | −0.76274 | 0.017793 | −0.93429 | 0.092081 | 5.03E−01 |
| ZNF703 | 1.23E−02 | −0.32601 | 0.000744 | −0.14954 | 0.366064 | 1.22E−17 |
| ZNRF3 | 1.40E−09 | −0.03445 | 0.605797 | −0.33884 | 0.002065 | 5.21E−29 |

TABLE 12

P values Correlating Gene Expression with MSS v. MSI, DSS, DFS, & Tumor
vs. Normal/Cox-regression for DSS & DFS

| Gene | MSS v. MSI-M.W.pv | DSS-Cox beta | DSS-Cox pv | DFS-Cox beta | DFS-Cox pv | T v. N-M.W.pv |
|---|---|---|---|---|---|---|
| MPDZ | 4.47E−01 | 0.079568 | 0.406857 | 0.657405 | 3.98E−05 | 0.034502 |
| DUSP14 | 8.90E−04 | 0.207902 | 0.047604 | 0.709569 | 0.000159 | 1.02E−35 |
| SCEL | 4.66E−01 | 0.081094 | 0.202236 | 0.301113 | 0.000357 | 3.82E−08 |
| ANXA2P2 | 1.39E−10 | 0.478663 | 0.003259 | 0.997702 | 0.000504 | 3.41E−03 |
| GLIS3 | 4.23E−01 | 0.0916 | 0.210004 | 0.397791 | 0.000566 | 1.39E−01 |
| DOK5 | 0.875129 | 0.105512 | 0.369053 | 0.577502 | 0.002218 | 0.823477 |
| VLDLR | 1.04E−02 | −0.00629 | 0.92868 | 0.323607 | 0.004972 | 5.44E−18 |
| CDC42BPA | 0.260157 | 0.032966 | 0.690294 | 0.401718 | 0.005473 | 9.47E−08 |
| USP32 | 7.89E−04 | 0.162429 | 0.221638 | 0.586012 | 0.01236 | 9.42E−01 |
| PITPNC1 | 1.36E−07 | 0.257758 | 0.029048 | 0.418362 | 0.026674 | 2.06E−06 |
| SEMG1 | 8.73E−09 | 0.098826 | 0.043099 | 0.153704 | 0.061048 | 4.94E−01 |
| SMU1 | 1.01E−11 | 0.36857 | 0.008896 | 0.016381 | 0.942047 | 1.95E−12 |
| ING1 | 2.09E−02 | 0.461934 | 0.020587 | 0.127394 | 0.710857 | 5.99E−05 |

It is to be understood that the present invention is not limited to the embodiments described above, but encompasses any and all embodiments within the scope of the following claims.

We claim:

1. A method for assessing the risk for metastatic relapse in early stage colorectal cancer (CRC) patients and for treating the patients diagnosed with metastatic forms of CRC, comprising the steps of:
   identifying patients with early stage CRC;
   establishing a control value of non-tumor tissue from the patients with early stage CRC;
   taking a biological sample from each of the patients, wherein the biological sample is selected from the group consisting of tissue biopsies, whole blood, plasma, serum, saliva, cell culture, and cerebrospinal fluid;
   simultaneously measuring a copy number level of thirteen metastasis inducing genes and twenty-nine metastasis suppressor genes in the biological sample from the patients;
   comparing the level of the metastasis inducing genes and the metastasis suppressor genes with the control value, wherein the level of the metastasis inducing genes and the metastasis suppressor genes is determined by using a technique selected from the group consisting of microarray, polymerase chain reaction (PCR), fluorescent in situ hybridization, comparative genomic hybridization (CGH), and array CGH;

determining the risk of metastatic relapse of metastatic risk in early stage CRC patients if a copy number gain in any one of the metastasis inducing genes is detected and a copy number loss in any one of the metastasis suppressor genes is detected; and administering chemotherapy to the patients determined to have a copy number gain in any one of the metastasis inducing genes and a copy number loss in any one of the metastasis suppressor genes;

wherein the thirteen metastasis-inducing genes include CDC42BPA, VLDLR, GLIS3, MPDZ, SMU1, ANXA2P2, SCEL, DUSP14, USP32, PITPNC1, SEMG1, DOK5, and ING1, and wherein the twenty-nine metastasis-suppressor genes include ZNF366, C5orf48, CSMD1, NAT1, NAT2, SPAG11A, ADRA1A, EPHX2, ZNF703, BRF2, RAB11FIP1, ADRB3, WDR5, DIO3, ONECUT1, C20orf202, SIRPD, ADRA1D, MCM8, LOC339593, GP1BB, CABIN1, TOP1P2, ZNRF3, KIAA1656, APOBEC3D, CACNA1I, FAM83F, and PCDHGA11.

2. The method for treating a patient diagnosed with colorectal cancer (CRC) according to claim 1, wherein the copy number is measured by hybridization to an array of nucleic acid probes.

3. The method for treating a patient diagnosed with colorectal cancer (CRC) according to claim 1, wherein:
the step of detecting a copy number level of the metastasis inducing genes and the metastasis suppressor genes in a biological sample from the patient includes measuring a gene expression product of the metastasis-inducing genes metastasis suppressor genes.

4. The method for treating a patient diagnosed with colorectal cancer (CRC) according to claim 3, wherein the gene expression product is mRNA and the level of the gene expression product is measured by hybridization to an array of nucleic acid probes or by quantitative PCR.

5. The method for treating a patient diagnosed with colorectal cancer (CRC) according to claim 3, wherein the gene expression product is protein and the level of the gene expression product is measured using immunohistochemistry, Western blotting, or ELISA (enzyme-linked immunosorbent assay).

* * * * *